US006244270B1

(12) United States Patent
Lutian et al.

(10) Patent No.: US 6,244,270 B1
(45) Date of Patent: Jun. 12, 2001

(54) HEAD IMMOBILIZER APPARATUS FOR USE WITH A SPINE BOARD

(75) Inventors: Kent L. Lutian, Elkhart, IN (US); Raymond Gallatin, Hartland; Harold Kahn, Fenton, both of MI (US)

(73) Assignee: Bremen Corporation, Bremen, IN (US)

(*) Notice: Subject to any disclaimer, the term of this patent is extended or adjusted under 35 U.S.C. 154(b) by 0 days.

(21) Appl. No.: 09/313,062

(22) Filed: May 17, 1999

(51) Int. Cl.[7] ................................................. A61B 19/00
(52) U.S. Cl. ............................... 128/869; 128/870; 5/637
(58) Field of Search ................................... 128/845, 846, 128/869, 870, 876; 5/630, 636, 637, 638

(56) References Cited

U.S. PATENT DOCUMENTS

| 4,297,984 | * | 11/1981 | Bashaw | 128/870 |
| 4,794,656 | | 1/1989 | Henley, Jr. | 5/82 |
| 5,207,716 | * | 5/1993 | McReynolds | 128/820 |
| 5,211,185 | | 5/1993 | Garth et al. | 128/870 |
| 5,265,625 | | 11/1993 | Bodman | 128/869 |
| 5,657,766 | | 8/1997 | Durham | 128/870 |
| 5,944,016 | * | 8/1999 | Ferko | 128/870 |
| 5,947,981 | * | 9/1999 | Cosman | 128/869 |

* cited by examiner

Primary Examiner—Michael A. Brown
(74) Attorney, Agent, or Firm—Young & Basile, PC

(57) ABSTRACT

A head immobilizer apparatus includes a base plate having mounting members on outer edges which are releasably engagable through apertures to a spine board. In one aspect, the mounting members are cantilevered clips include a first leg projecting downward from the plane of the base plate and an outwardly and upwardly extending second leg. Alternately, a pair of clips may be formed on each opposed side edge and one additional clip formed on one end edge of the base plate. A flange is disposed adjacent to at least one side edge of each clip and is unitarily formed as part of the base plate. Each flange extends outward for substantially the same length as the adjacent clip to sandwich an outer edge of the spine board therebetween under spring force generated by the resilient, cantilever clips. In another aspect, the mounting members are hook shaped legs depending from a bottom surface of the base plate and terminating in projections extending from an end of each leg to form a hook shaped recess engagable with an edge of the spine board adjacent one aperture in the spine board to releasably mount the base plate to the spine board. Mating hook and loop fastener strips are mounted on the base plate and the underside of a pair of head pads for selectively positioning the head pads on the base plate on opposite sides of a victim's head. At least one head and/or chin strap is releasably mountable to hook and loop strips carried on the outer surfaces of each head pad.

27 Claims, 8 Drawing Sheets

HEAD IMMOBILIZER APPARATUS FOR USE WITH A SPINE BOARD

BACKGROUND OF THE INVENTION

1. Field of the Invention

Present invention relates, in general, to head immobilization apparatus and, more specifically, to head immobilization apparatus which are attachable to spine or back boards.

2. Description of the Art

In accidents involving apparent injury to the head, neck and/or spine, the head and cervical spine areas of the accident victim are routinely immobilized to prevent further injury during transport to a medical care facility. Rigid spine or back boards are typically used to support the victim who is lifted or transferred onto the board. Stiff pillows or blocks are placed tightly on either side of the victim's head. One or more head and/or chin straps are then tightly secured over the pillows to fixedly hold the victim's head in place. The pillows or blocks can be selectively placed on the spine or back board at variable spacings to accommodate different sized victims' heads.

One typical prior art head immobilizer used with a conventional spine or back board is shown in FIGS. 1 and 2. The head immobilizer 10 includes a substantially rigid base panel 12 formed of a rigid foam and vinyl material. A pad or raised center portion 14 is mounted centrally on the base panel 12. A plurality of hook and loop fastening strips 16 are attached to the base panel 12 and extend laterally from the raised center portion 14. A pair of straps 17, each with a D-hook 18 at one end, are stitched or otherwise securely mounted to the underside of the base panel 12. The D-hooks 18 interact with the ends of anchor straps 20 attached to the underside of the opposite end of the base panel 12 to secure the base panel 12 about one end of a spine or back board 23. The straps 17 or 20 may pass through apertures 24 formed along the sides of the spine board 23.

A pair of pillows 26, each with an ear aperture 28, have a generally wedge shape and are provided with mating hook or loop VELCRO-type fasteners on the underside for engagement with the fastener strips 16 on the underside of the base panel 12. This enables the pillows 26 to be wedged tightly against opposite sides of the victim's head. The pillows 26 are typically formed of a PVN foam having a PVC or vinyl coating applied to the exterior surface of the foam.

A pair of head straps 32, each carrying a D-hook 32 at an outer end, are secured to the underside of the base panel 12 adjacent one end of the base panel 12. The D-hooks 32 interact with opposite ends of a head strap 34 which extends through a central pad 36. The pad 36 is engaged with the victim's forehead and the straps 34 tightened through the D-hooks 32. A similar pair of chin straps 38, each also having a D-hook 40 at an outer end, interact with opposite ends of a chin strap 42 which extends outward from opposite ends of a chin pad 44. The straps 42 are tightened through the D-hooks 40 to securely hold the victim's chin between the pillows 26.

Serious injuries frequently involve the discharge of blood and other fluids from a victim which can contaminate the spine board 23 as well as various components of the head immobilizing apparatus 10. It then becomes necessary to sanitize both the spine board 23 and all of the components of the head immobilizing apparatus 10. This is difficult for the rather large spine board as well as the various flexible straps and large pillows employed on the head immobilizing apparatus.

While this particular head immobilizing apparatus and spine board can effectively immobilize a victim's head, it is not without deficiencies relating to cost of manufacture, easy reuse, and easy cleaning or sanitizing after each use.

Thus, it would be desirable to provide a head immobilizing apparatus for use with a spine or back board which overcomes the deficiencies of previously devised head immobilizing apparatus. It would also be desirable to provide a head immobilizing apparatus which can be manufactured with a sufficiently low cost so as to make a one time use and subsequent discarding cost effective. At the same time, it would be desirable to provide a head immobilizing apparatus which can be easily cleaned and sanitized, if necessary. It would also be desirable to provide a head immobilizing apparatus which can be quickly and easily attached to a spine board.

SUMMARY OF THE INVENTION

The present invention is a head immobilizing apparatus for use with a spine or back board.

In one aspect, the head immobilizer apparatus includes a base plate having opposed top and bottom surfaces and spaced side edges. A pair of head pads are removably attachable to the top surface of the base plate in registry with opposed sides of a victim's head for restricting movement of the victim's head relative to the spine board. For added immobilization, one or more straps extend across the head pads for immobilizing the patient's head between the head pads. Finally, mounting members, unitarily carried on the base plate, releasably attach the base plate to the spine board through apertures in the spine or back board.

Preferably, the base plate is concave in shape between the opposed side edges to provide a spring force in conjunction with the mounting members to securely fix the base plate on the spine board.

Mating hook and loop material strips are mounted on the top surface of the base plate and the bottom surface of the head pads for releasably securing the head pads to the base plate in any selected spaced position to fit the head pads snugly against opposite sides of a victim's head to immobilize the head.

The straps preferably comprise at least one and preferably two straps carrying hook and loop material strips at opposite ends which are releasably engagable with hook and loop strips carried on the outer surfaces of the head pads.

The mounting members, in one aspect of the invention, preferably comprise at least one clip cantilevered from each side edge of the base plate and, optionally, from one end edge of the base plate. In one embodiment, a pair of clips are mounted on each side edge of the base plate. Each clip is formed of a first leg unitarily attached to and depending from a side edge of the base plate. A second leg extends angularly from the first leg, preferably, at an acute, upward angle.

A flange projects unitarily from the base plate adjacent to each clip and cooperates with each clip to fixedly secure the base plate to a spine board by sandwiching the spine board between each cooperating flange and clip pair.

In another aspect of the present invention, the base plate remains concave in shape between opposed side edges or at least upward angled at the side edges with respect to a center portion of the base plate to provide a spring force allowing movement of the side edge portions of the base plate and the mounting members carried thereon as well as separate movement of a mounting member mounted on the top end of the base plate. In this aspect of the invention, the mounting members are formed as hooks including a leg depending, preferably integrally, from the bottom surface of the base plate and terminating in an inboard extending projection at the end of the leg, which projection extends toward the center longitudinal axis of the base plate. The mounting member on the top end of the base plate has a similar hook shape formed of a depending leg and a projection extending toward the opposed bottom end of the base plate.

The mounting members are insertable through apertures along the side edges and at the top end of a spine board and engage the inner edge of the spine board adjacent to each aperture. The over bending of the concave or angled base plate causes the hooks to be biased into the spine board to securely mount the base plate on the spine board; while at the same time enabling its easy removal for cleaning, replacement, etc., after each use.

The head immobilizer apparatus of the present invention provides significant advantages over previously devised head immobilizer apparatus utilized with the spine or back boards. The present head immobilizer apparatus is releasably attachable to a spine or back board without the need for interconnecting straps and hooks. This simplifies the mounting and dismounting of the back plate of the head immobilizer apparatus with respect to a spine board. In addition, the minimal number of components used to form the head immobilizer apparatus enables a low manufacturing cost. As a result, the present head immobilizer apparatus can be discarded after each use without a significant cost penalty. Alternately, if it is desired to reuse the head immobilizer apparatus of the present invention, the apparatus can be easily cleaned and sanitized, again due to the minimal number of separate components and, in particular, components such as fabric straps which absorb greater quantities of blood and other fluids.

BRIEF DESCRIPTION OF THE DRAWING

The various features, advantages and other uses of the present invention will become more apparent by referring to the following detailed description and drawings in which.

DESCRIPTION OF THE PREFERRED EMBODIMENTS

Figure 1:
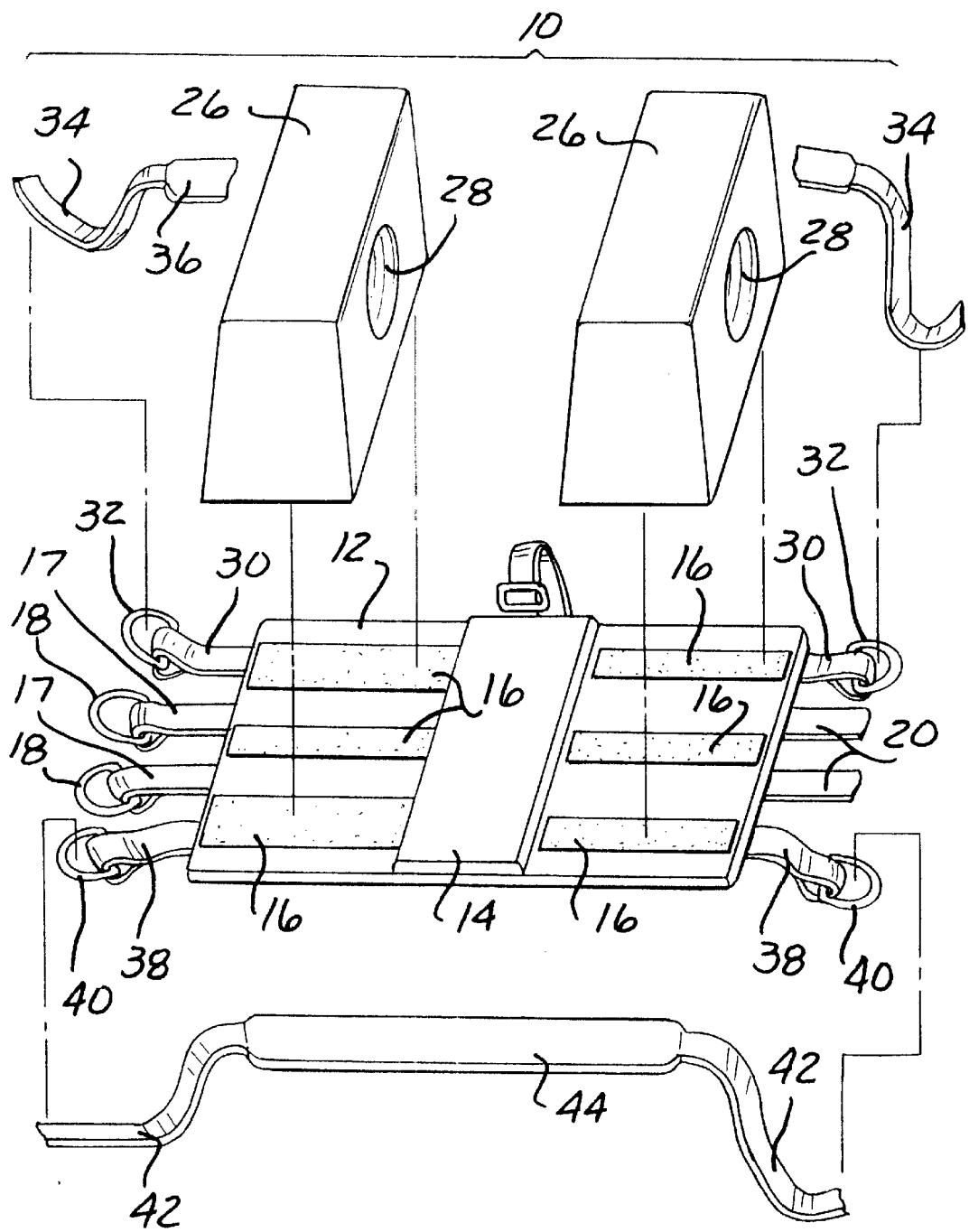
FIG. 1 is an exploded perspective view of a prior art head immobilizing apparatus.
Figure 2:
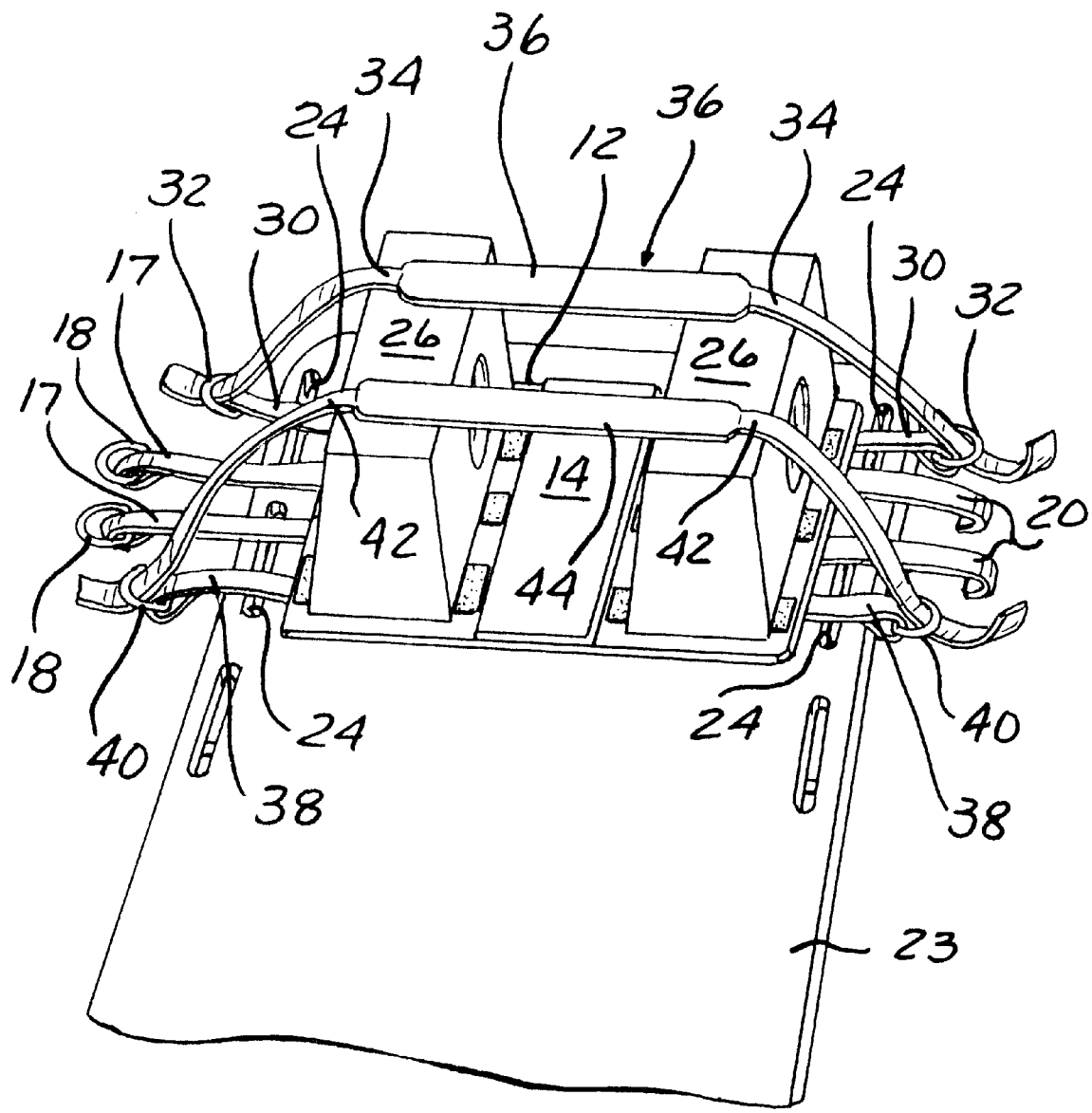
FIG. 2 is an exploded perspective view of the head immobilizing apparatus of FIG. 1 mounted on one end of a spine or back board.

Referring now to the drawings and to FIGS. 36, in particular, there is depicted a first embodiment of a head immobilizer apparatus 50 according to the present invention. The apparatus 50 includes a base plate 52 formed of a rigid, but still flexible plastic material. Preferably, polyethylene or other suitable plastic may be employed to form the base plate 52.

Figure 3:
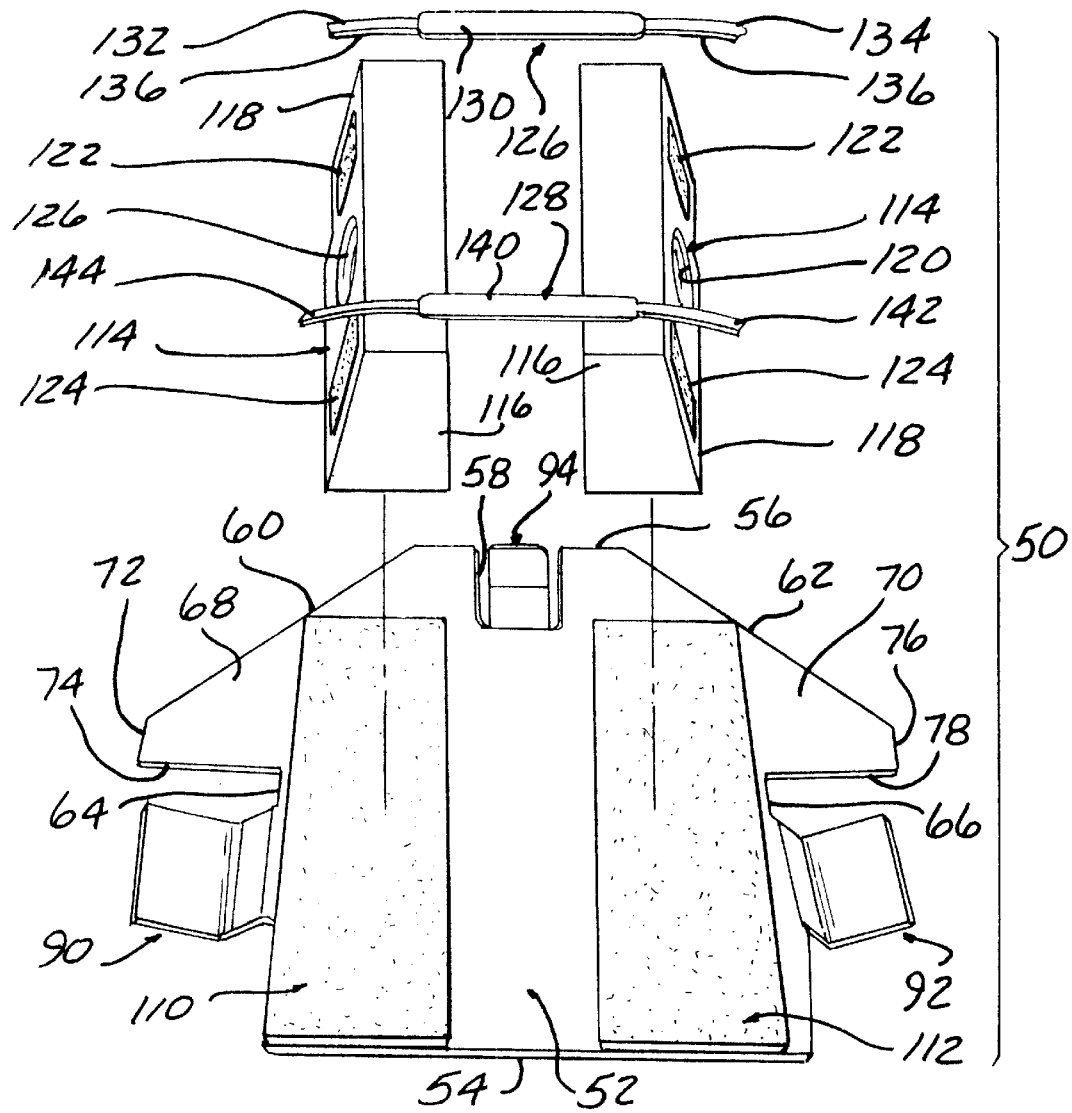
FIG. 3 is an exploded perspective view of a first embodiment of a head immobilizing apparatus of the present invention.

As shown in FIG. 3, the base plate 52 has a first end 54 and an opposed second end 56. The first end 54 has a generally planar edge. The opposed second end 56 also has a planar edge separated by a central cutout 58, the purpose of which will be described in greater detail hereafter. A pair of side edges 60 and 62 extend angularly from opposite ends of the second end 56. Similarly, side edges 64 and 66 extend perpendicularly from opposite ends of the first end, 54. A pair of mounting flanges 68 and 70 are formed intermediately between the side edges 60 and 64, and the side edges 62 and 66, respectively. Each of the mounting flanges 68 and 70 has an end formed as a continuation of one side edge 60 or 62. For example, an outer end 72 extends between one end of the angled side edges 60 and an edge 74 extending perpendicularly from the side edge 64. Similarly, an outer end 76 extends angularly from the side edge of 62 and is located intermediately between the side edge 62 and an edge 78 extending perpendicularly from the side edge 66. The mounting flanges 68 and 70 lie in the general plane of the base plate 52. Preferably, the entire base plate 52 has a concave shape between the mounting flanges 68 and 70. This provides a spring force to the base plate 52 when it is bent to a planar shape when mounted on a spine board as described hereafter.

Mounting members are provided for mounting the base plate 52 in apertures 80, 82 and 84 located along the side and end edges of a spine board 86. Preferably, the mounting members, denoted generally by reference numbers 90 and 92, comprises at least two clips in combination with the mounting flanges 68 and 70. Optionally, an additional mounting member 94 is formed along the second end 56 of the base plate 52 within the cutout 58.

Figure 4:
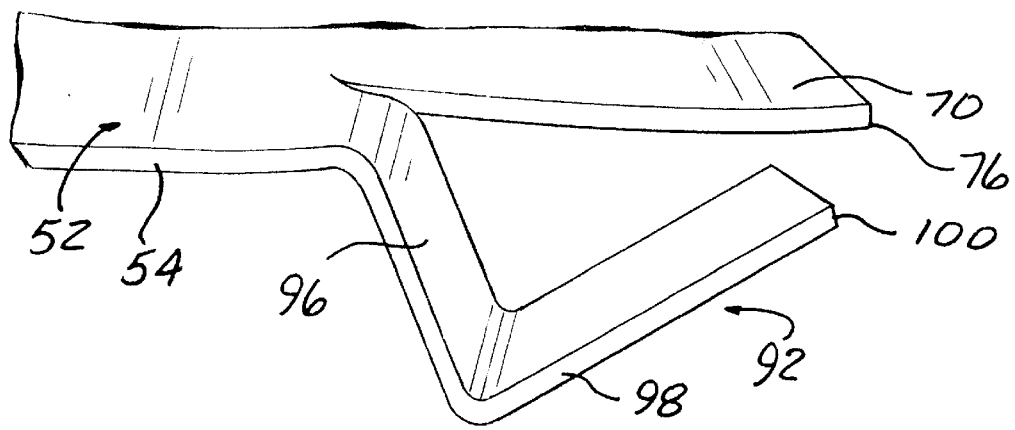
FIG. 4 is a partial, right hand, end elevational view of the base panel shown in FIG. 4.
Figure 5:
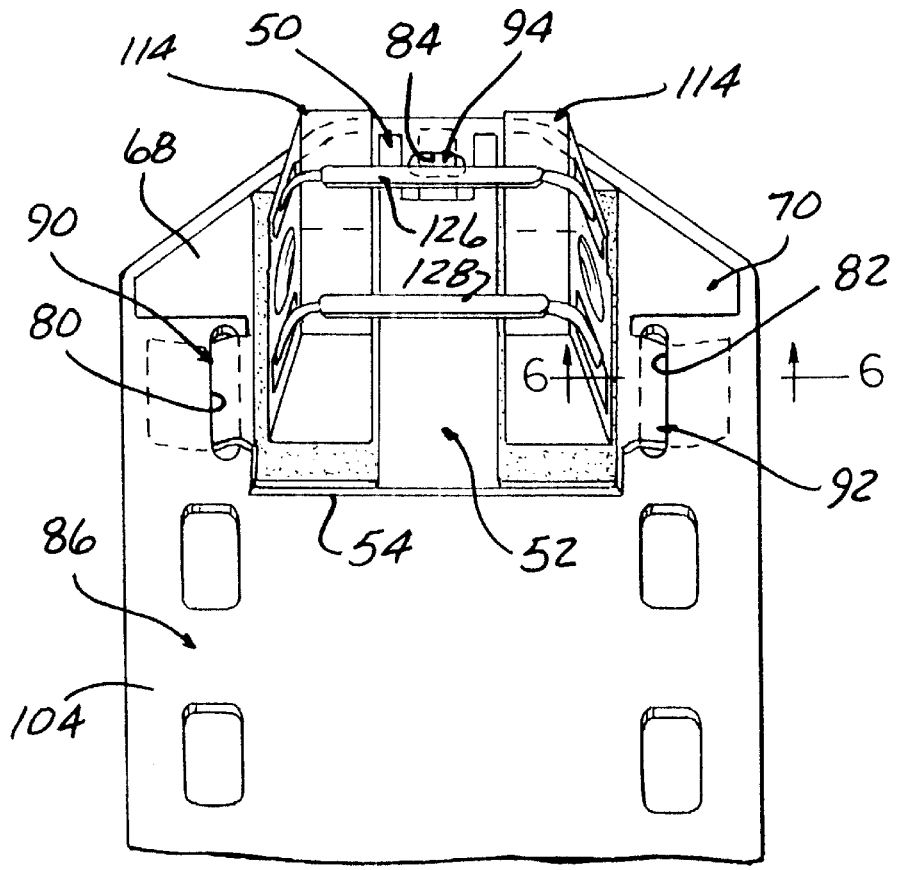
FIG. 5 is a plan elevational view of the head immobilizer apparatus shown in FIGS. 3 and 4 mounted on a spine board.
Figure 6:
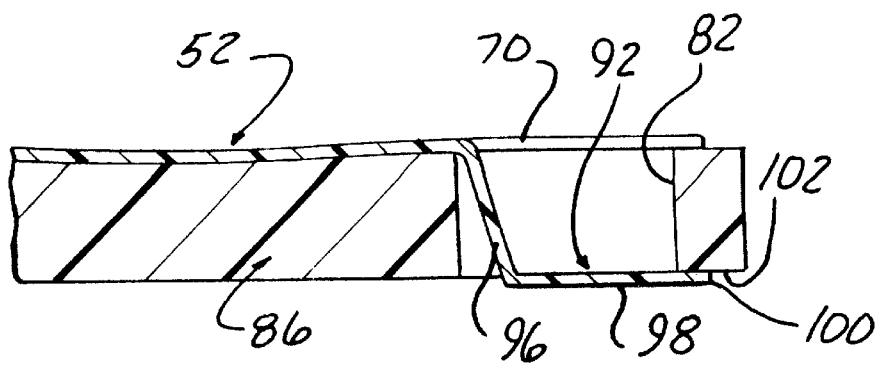
FIG. 6 is a cross-sectional view generally taken along line 6—6 in FIG. 5.

As shown in greater detail in FIGS. 3, 4 and 6, each mounting member 90, 92 and 94 is identically constructed. Thus, the following description of mounting member 92 will be understood to apply equally to the other mounting means 90 and 94.

As shown in FIGS. 3, 4, 5 and 6, the mounting member 92 is in the form of a cantilevered clip which projects outwardly from the side end 66 of the base plate 52, generally, adjacent to the first end 54. The clip 92 is formed of a first leg 96 which projects angularly from the plane of the base plate 52 generally downward below the back surface of the base plate 52. A second leg 98 projects angularly from the outer end of the first leg 96 in a generally upward or acute angle and terminates in an outer end 100. As shown in FIG. 4, the outer end 100 of the second leg 98 is disposed in proximity with the outer side edge 76 of the mounting flange 70, but is spaced a short distance therefrom in both horizontal and vertical directions.

In order to mount the base plate 12 to the spine board 86, one of the mounting clips 90, 92, or 94 is initially inserted into its corresponding aperture 80, 82 or 84 in the spine board 86. The remaining clips 90, 92 and 94 are then inserted into an apertures 80, 82 and 84, by way of example only.

For example, the second leg 98 of the mounting member or clip 92 is inserted through the aperture 82 in the spine board. The base plate 52 is pivoted about the legs 96 and 98 of the mounting means or clip 92 until the outer end 100 of the second leg 98 engages the bottom surface 102 of the spine board 106 on the outboard side of the aperture 82 as shown in FIG. 6. The spine board 52 is then bent convexly past the concave curvature of the base plate 52 while inserting the mounting member 94 and then the mounting member 90 into the respective apertures 84 and 80 in the spine board 82. When all three mounting members, 90, 92 and 94, are inserted into the respective apertures, 80, 82 and 84, in the spine board 86, the base plate 52 assumes a generally planar configuration in substantially complete surface contact with the upper surface of the spine board 86. However, the original concave shape of the base plate 52 imparts a spring force in a direction upward from the upper or top surface of the spine board 86 which, in conjunction with the spring force generated between the sandwich effect of each clip 90, 92 and 94 and its adjacent flange, holds the second legs 98 of each of the mounting members or clips, 90, 92 and 94 in fixed engagement with the bottom surface 102 of the spine board 86 to rigidly and stationarily hold the base plate 52 on the spine board 86 without the need for additional mounting straps.

With the base plate 52 securely mounted on one end of the spine board 86, the victim may then be lifted or otherwise placed on the spine board 86 with the victim's head laying on the base plate 52.

As shown in FIG. 3, a pair of hook or loop fastener strips 110 and 112 are mounted, such as by adhesive, on the base plate 52 and extend longitudinally between the first and second ends 54 and 56 of the base plate 52.

The victim's head is preferably centrally positioned on the base plate 52. A pair of head pads, pillows or blocks 114 are securely positioned in tight conformity on opposed sides of the victim's head. Each head pad 114 has a generally wedge or triangular shape formed of a planar inner surface 116 and an angular opposed, outer surface 118. Although not shown in FIG. 3, mating hook or loop fasteners are mounted on the bottom surface of each head pad 114 for secure; but releasable engagement with mating fastener strips 110 and 112 on the base plate 52 to securely position the head pads 114 on the base plate 52 at any desired width or spacing to accommodate any size head. A centrally located aperture 120 is preferably formed in each head pad 114 to expose the victim's ear.

For added head immobilization, a pair of hook or loop fastener strips 122 and 124 are mounted on the outer surface 118 of each head pad 114 for receiving at least one and, preferably, two straps, namely a head strap 126 and a chin strap 128, respectively. The head strap 126 includes a central pad 130 with a continuous or two separate straps 132 and 134 projecting outwardly from opposite ends. Mating hook or loop fastener strips 136 are mounted on the underside of each strap or strap end 132 and 134. This enables the head strap 126 to be tightly secured between the spaced head pads 114 with the pad 130 on the head strap 126 in tight engagement with the victim's forehead.

Similarly, the chin strap 128 includes a central pad having outwardly extending straps or opposite ends 142 and 144 of a single continuous strap, each with hook or loop strips on an underside surface for engagement with the mating strips 124 on the head pads 114. This enables the chin strap 128 to be tightly secured across the head pads 114 with the pad 140 in secure engagement with the victim's chin thereby completely immobilizing the victim's head.

Thus, the head immobilizer apparatus 50 can be easily secured to a spine board 86 and, due to the minimal number of separate components, can be easily and quickly positioned about a victim's head to immobilize the victim's head. The minimal number of separate components simplifies the task of cleaning and sanitizing the head immobilizer apparatus 50 after each use or enables the entire head immobilizer apparatus 50 to be discarded after each use without a significant cost penalty.

Figure 7:
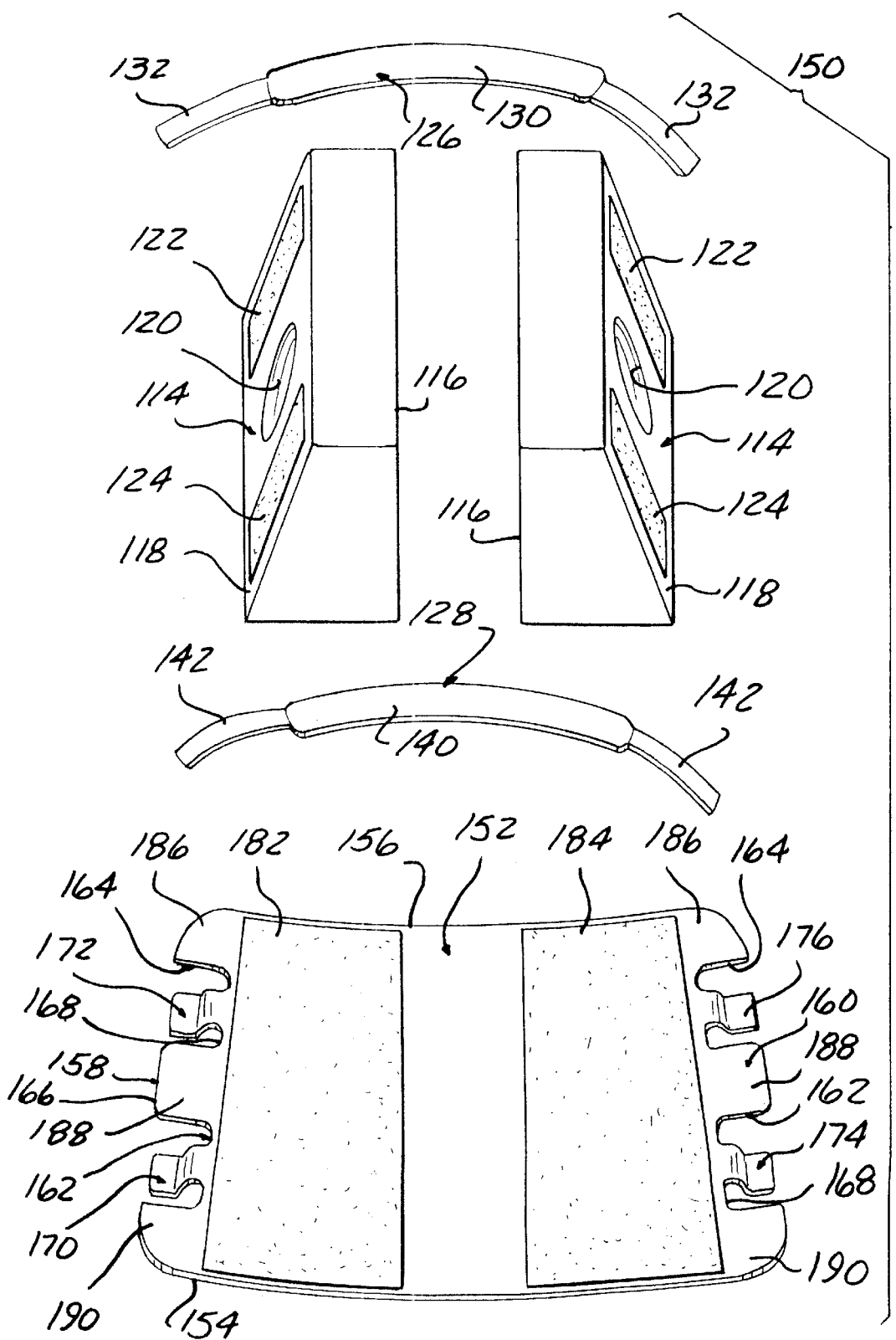
FIG. 7 is an exploded, perspective view of a second embodiment of a head immobilizer apparatus according to the present invention.
Figure 8:
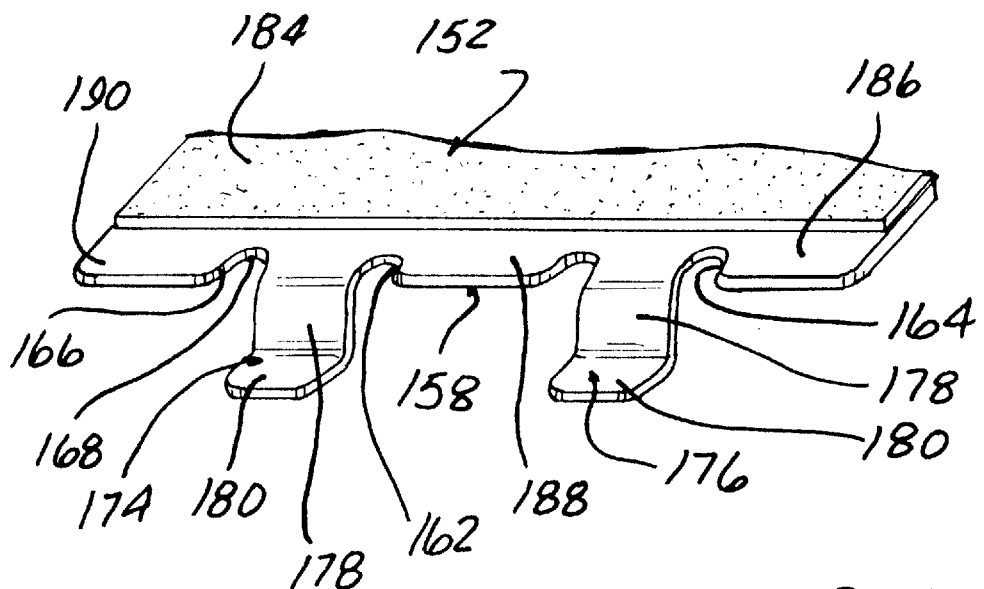
FIG. 8 is a right-hand, side elevational view of the base panel shown in FIG. 7.
Figure 9:
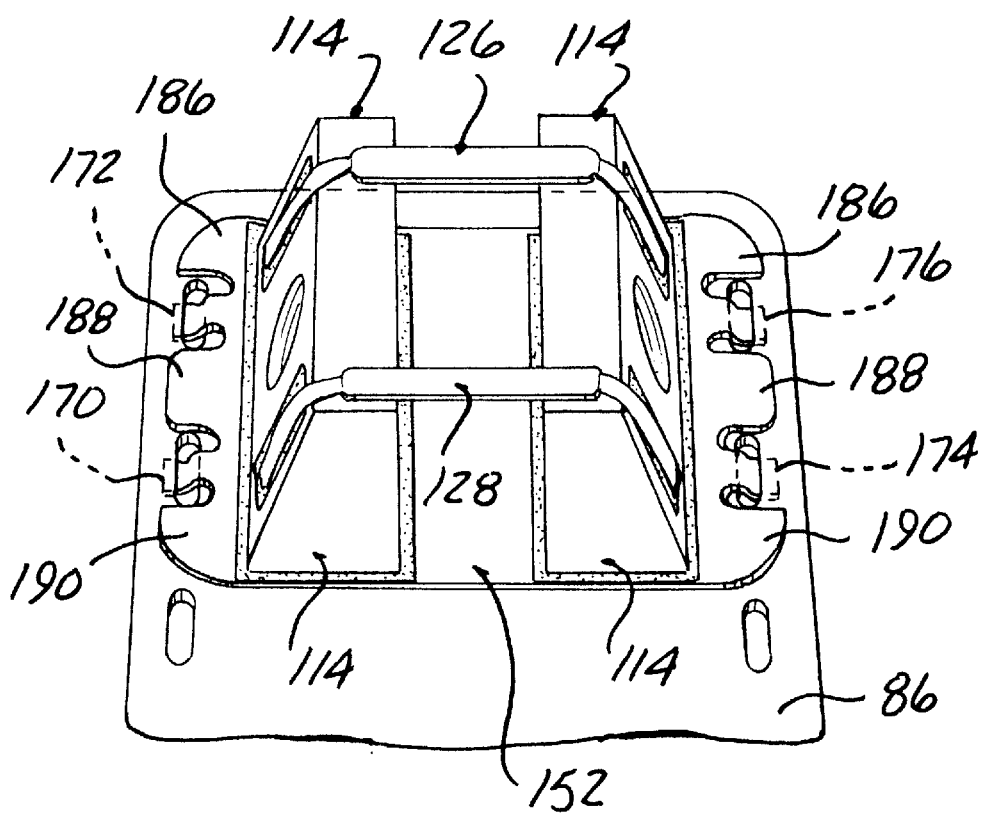
FIG. 9 is a plan elevational view showing the head immobilizer apparatus of FIGS. 7–9 mounted on a spine board.

Another embodiment of a head immobilizer apparatus 50 is shown in FIGS. 7–9. The head immobilizer apparatus 150 is substantially identical to the head immobilizer apparatus 50 described above and shares common components, such as the head strap 126, the chin strap 128 and the head pads 114. Further, while base plate 152 differs somewhat in configuration from the base plate 52 of the head immobilizer apparatus 50, the function of the base plate 152 is the same insofar as its use and mounting on a spine board 86.

In this embodiment, the base plate 152 is also formed of a plastic material, such as polyethylene, for example. The base plate 152 has substantial rigidity, but is capable of flexing about a longitudinal center line. The base plate 152 has a concave shape between opposed side edges as described hereafter.

The base plate 152 is formed with opposed first and second ends 54 and 156. The first and second ends 154 and 156 are interconnected by opposed side edges 158 and 160. By way of example only, each side edge 158 and 160 is formed of a plurality of notches 162 and 164 which extend inward toward the center of the base plate 152 from an outer edge 166 to an inner end 168. A mounting means or clip is interposed within each notch 162 and 164. By way of example only, four mounting members or clips 170, 172, 174, 176 are unitarily formed on the base plate 152, with one clip 170, 172, 174 and 176 disposed in one of the notches 162 and 164.

The notches 162 and 164 on each side edge 158 and 160 of the base plate 152 form a plurality of flanges 186, 188 and 190. Two of the flanges are adjacent to each clip 170, 172, 174 and 176.

Each mounting clip 170, 172, 174 and 176 is identically constructed to the mounting clips 90, 92 and 94 described above and shown in FIGS. 3 and 4. Thus, the mounting members or clips 174 and 176 shown in FIG. 8 are formed with a first leg 178 which is unitarily formed with and project downwardly and at an outward angle, generally, from the inner edge 168 of each notch 162 or 164. A second outwardly extending, angularly disposed leg 180 extends from one end of the first leg 178.

The overall mounting and use of the base plate 152 is identical to the base plate 52 described above except that the mounting means 174 and 176 on the right side of the base plate 152 are inserted into separate apertures on the spine board 86 prior to overbending the concave-shaped base plate 152 to bring the opposed mounting clips 170 and 172 into corresponding apertures on the opposite side of the spine board 86. Release of the overbending force on the base plate 152 enables the outer ends of each of the second legs 180 of each of the mounting clips 170, 172, 174 and 176 to slide into secure engagement with the bottom surface of the spine board 86 and to generate a spring force to securely maintain the base plate 152 on the spine board 86 without the need for additional mounting straps as in prior art head immobilizer apparatus.

A pair of longitudinally extending hook or loop strips 182 and 184 are secured by means of adhesive to the upper surface of the base plate 152 and mate with corresponding hook or loop strips on the bottom surface of each head pad 114 as described above to enable the head pads 114 to be laterally and longitudinally positioned at any desired location with respect to each other about an interposed victim's head. The head and chin straps 126 and 128 are then extended across and secured to fastener strips 122 and 124 on each head pad 114.

It will be understood that either or both of the head strap or chin strap 126 and 128 may be lengthened so as to enable each strap 126 and 128 to completely encircle the entire spine board 86 and connect to the fastener strip 122 on the opposite head pad 114.

Referring now to FIGS. 10–13, there is depicted another aspect of the present invention in which an alternate embodiment of a base plate 200 is shown. The base plate 200, while having a slightly different configuration than the previously described base plate, nevertheless is fully functional with the head pads or pillows and the chin straps used in the previously described embodiments of the present invention.

As shown in FIGS. 10–13, the base plate 200 is formed of a thin sheet having first and second ends 202 and 204, opposed side edges 206 and 208, and angled edges 210 and 212 extending from the first end 204 to intermediate edges 214 and 216, respectively, which extend between one end of each angled edge 210 and 212 and one end of one of the side edges 206 and 208. The intermediate edges 214 and 216 are generally parallel to the bottom end 202.

Figure 10:
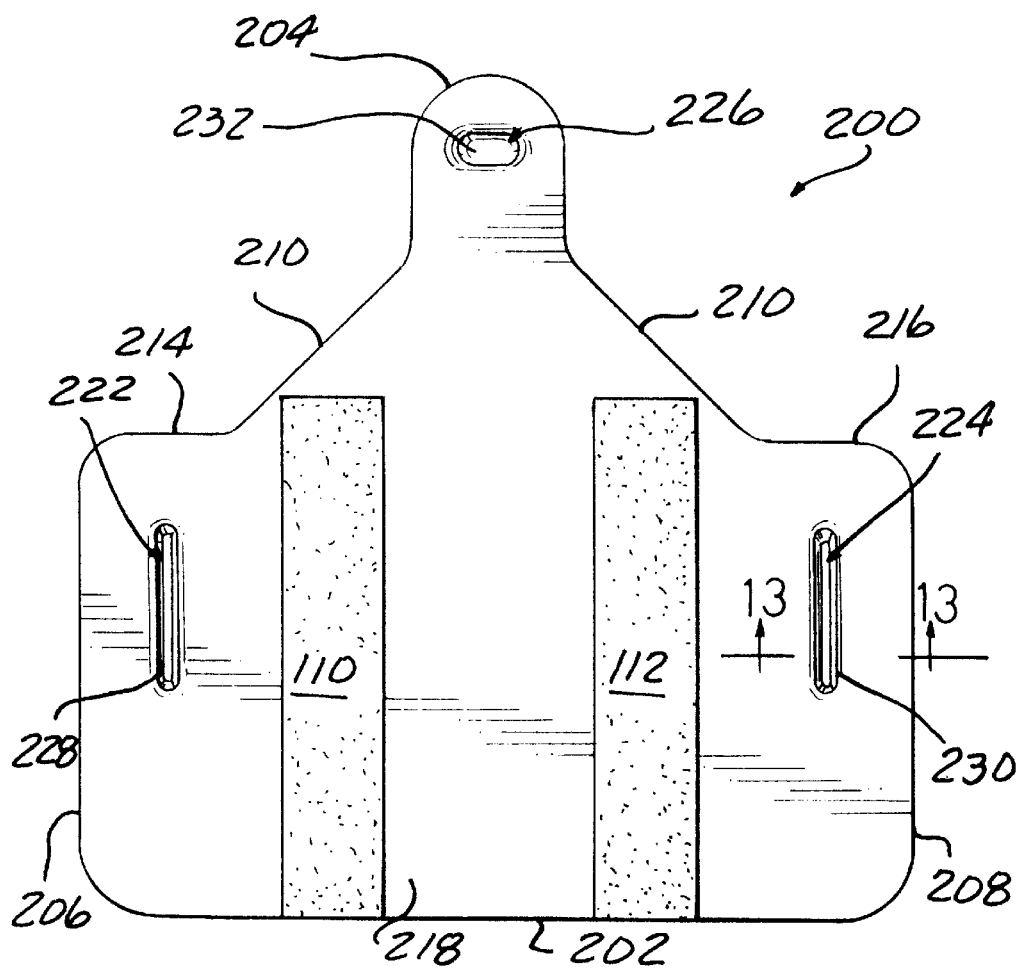
FIG. 10 is a top plan view of another embodiment of a base plate according to the present invention.
Figure 11:
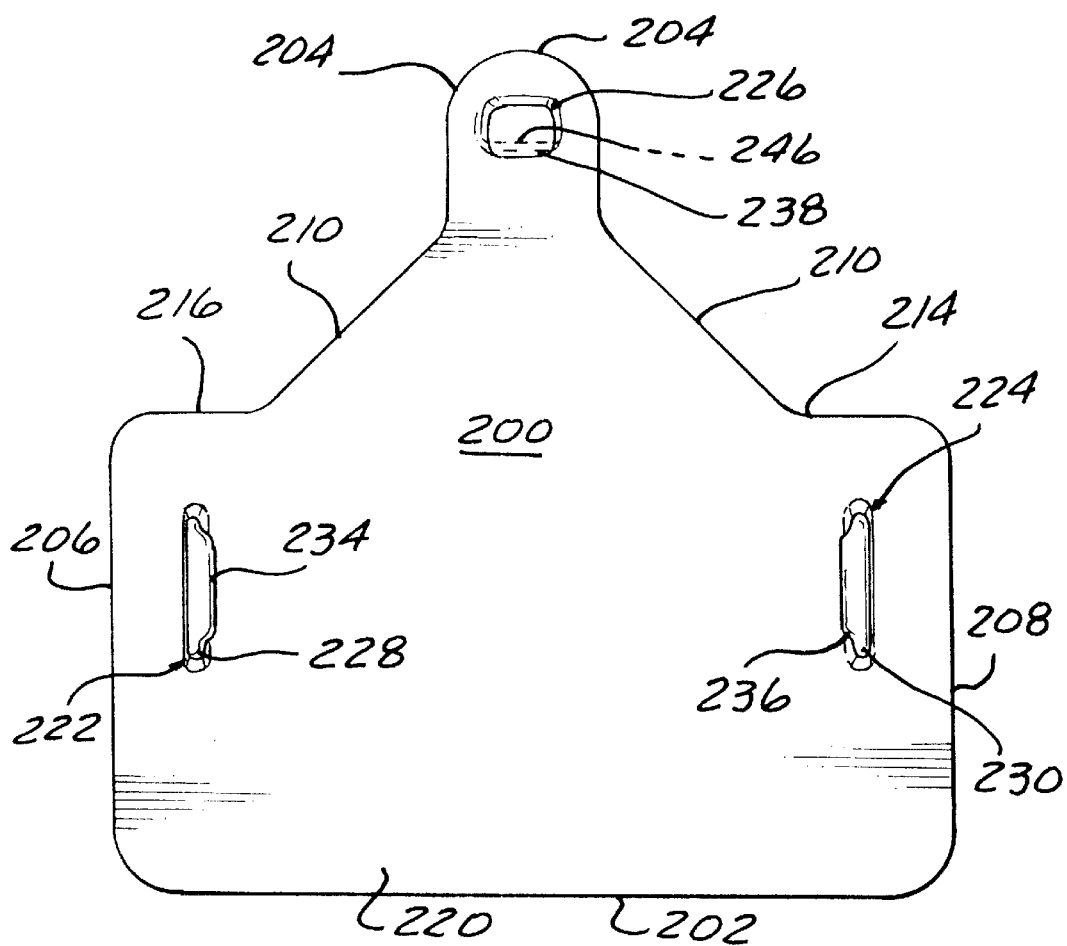
FIG. 11 is a bottom elevational view of the base plate shown in FIG. 10.

The base plate 200 is also formed with opposed major surfaces including a top surface 218 shown in FIG. 10 and an opposed bottom surface 220 shown in FIG. 11.

Figure 12:
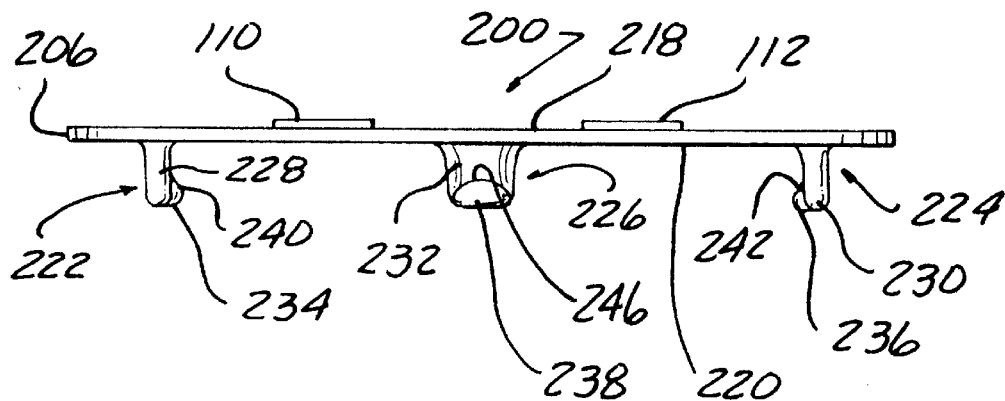
FIG. 12 is a lower end view of the base plate shown in FIGS. 10 and 11.

As clearly shown in FIG. 12, the base plate 200 is formed with a slight concave curvature extending completely between the side edges 206 and 208. Similarly, the top end 204 projects or curves slightly out of the plane of the center axis of the base plate 200. Alternately, the side portions of the base plate 200 adjacent to each side edge 206 and 208 may be formed with a slight upward curvature or planar angle with respect to a flat center portion on the base plate 200. Thus, instead of the arcuate shape of the side edge portions adjacent each side edge 206 and 208, the side edge portions could be planar, but generally extending upward at an acute angle with respect to the bottom surface 220 of the base plate 200.

As in the previous base plates, the base plate 200 is formed with a rigid, but still flexible plastic material, such as polyethylene or other suitable plastics.

The mounting members in this aspect of the base plate 200 are formed as inward facing hooks. Although two side mounting members 222 and 224 may be exclusively employed, it is preferred that three mounting members, including the two side mounting members 222 and 224, and a top end mounting member 226 be used to securely, yet removably mount the base plate 220 to a spine board. Each mounting member 222, 224 and 226 is similarly formed and includes a depending leg portion 228 and 230 for the side mounting members 222 and 224, respectively, and a depending leg portion 232 for the top end mounting member 226. As shown in FIG. 1, each leg 228 is formed as a hollow member which is drawn or otherwise formed from the bottom surface 220 of the base plate 200 and extends from an open end at the top surface 218. The bottom portion of each leg 228, 230 and 232 includes an inward facing projection 234, 236 and 238, respectively, which is integrally formed with the legs 228, 230 and 232 and projects inward toward the longitudinal center axis of the base plate 200 in the case of the projections 234 and 236 on the side mounting members 222 and 224, respectively, and toward the bottom edge 202 in the case of the projection 238 on the top end mounting member 226.

Figure 13:
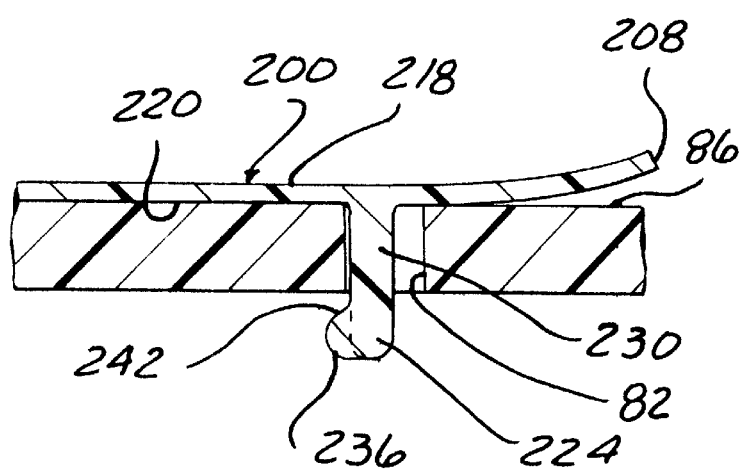
FIG. 13 is a cross-sectional view generally taken along line 13—13 in FIG. 11 and showing the mounting of the base plate to a spine board.

Due to the curvature or angle of each of the side edge portion and the top end portion of the base plate 200 with respect to the central portion of the base plate 200, the side edge portions and the top end portion, each of which carries one of the mounting members 222, 224 and 226, is separately movable with respect to the remaining portion of the base plate 200 to enable each leg and hook projection portion of each depending mounting member 222, 224 and 226 to be extended through one of the apertures in a spine board and snapped in place with a hook shaped recess 240, 242 and 244 engaging the inner edge of the spine board adjacent each aperture as shown more clearly in FIG. 13 for the mounting member 224.

It will be understood that the hollow construction of each mounting member 222, 224 and 226 described above and shown in FIGS. 10–13 is by way of example only. Alternate constructions for the hook shaped mounting members 222, 224 and 226 may also be employed. For example, solid hook shaped mounting members having the configuration generally shown in FIG. 12 may be injected molded as an integral, one-piece part of the base plate 200. Alternately, each mounting member 222, 224 and 226 may be separately formed as a discrete component and then unitarily attached to the bottom surface 220 of the base plate 200 by means of a high strength adhesive, mechanical fasteners, etc.

Finally, as shown in FIG. 10, mating hook and loop fastening strips, identical to the fastening strips 110 and 112 shown in FIG. 3, are mounted on the top surface 218 in the base plate 220, preferably by means of an adhesive. The fastening strips 110 and 112, which may be the loop type fasteners, releasably engage the mating hook fastening strips mounted on the bottom of the head pads or pillows to releasably mount the pillows to the base plate 200 as described above in the other embodiments of the present invention.

The use of the base plate 200 is identical to the use of the preceding base plates in that the base plate 200 is first placed on the spine board and the mounting members 222, 224 and 226 aligned with one of the apertures in the spine board. The side edge portions and the top end portion of the base plate 200 are then overbent against the curvature or angle of the side edges 206 and 208 and the top end 204 to insert the respective mounting members 222, 224 and 226 through the corresponding, aligned aperture in the spine board. The overbending force biases the hook shaped lower portions of each mounting member 222, 224 and 226 into engagement with an inner edge of the spine board adjacent to each aperture in the spine board to securely mount the base plate 200 and any head pads and chin straps releasably mounted thereon on the spine board.

Release of the base plate 200 from the spine board is a simple matter of merely bending each side edge 206 and 208 of the base plate 200 away from the spine board to release the hook shaped projection at the end of the leg of each mounting member 222 and 224 from the edge of the spine board enabling the mounting member 222 and 224 to be pulled through the respective apertures in the spine board. A similar release sequence is employed to separate the top end mounting member 226 from its corresponding aperture in the spine board.

In summary, there has been disclosed a unique head immobilizer apparatus for use with a spine or back board which provides significant advantages insofar as its use and reuse. The head immobilizer apparatus of the present invention is simply constructed with a minimal number of separate components as compared to prior art head immobilizing apparatus which contributes to a lower manufacturing cost. This enables the entire head immobilizer apparatus and all of its components to be discarded, if desired, after each use without a significant cost penalty. Furthermore, the minimum number of components also enables the head of the immobilizer apparatus to be easily cleaned and sanitized, if necessary, after each use.

The head immobilizer apparatus is mountable on a spine board by movable mounting members carried on the base panel or plate thereby eliminating the need for separate mounting straps affixed to the base panel which, in prior art apparatus, tightly encircled one end of a spine or back board. This enables the present head immobilizer apparatus to be easily and quickly attached to and removed from the spine board.

What is claimed is:

1. A head immobilizing apparatus for use with a spine board having peripheral apertures, the head immobilizing apparatus comprising:

a base plate having a top surface and spaced side edges;

head pad means removably attached to the base plate, for restricting movement of a victim's head; and first and second clips carried on opposite side edges of the base plate and projecting outwardly therefrom, the first and second clips removably mounting the base plate to a spine board through apertures in a spine board, the first and second clips each including:

a first leg attached to and depending from one side edge of the base plate; and a second leg extending angularly from the first leg.

2. The apparatus of claim 1 wherein the top surface of the base plate is concave.

3. The apparatus of claim 1 wherein the second leg extends at an acute angle with respect to the first leg.

4. The apparatus of claim 1 further comprising:

a flange projecting from the base plate in proximity to each of the first and second clips.

5. The apparatus of claim 4 wherein:

one flange and one of the first and second clips sandwich an edge of a spine board therebetween when the base plate is mounted on the spine board.

6. The apparatus of claim 4 further comprising:

a pair of flanges disposed on each side of each of the first and second clips.

7. The apparatus of claim 4 wherein each flange is unitarily formed with base plate.

8. The apparatus of claim 7 wherein:

the first and second clips are unitary with the base plate.

9. The apparatus of claim 4 when the first and second clips are unitarily formed with the base plate.

10. The apparatus of claim 1 wherein the base plate has a concave top surface.

11. The apparatus of claim 1 wherein the first and second clips further comprise:

a pair of first clips and a pair of second clips spaced apart on each side edge of the base plate.

12. The apparatus of claim 11 further comprising:

at least one flange projecting from the base plate in proximity with each of the first and second clips.

13. The apparatus of claim 1 wherein the head pad means comprises:

a pair of head pads.

14. The apparatus of claim 13 further comprising:

means for releasably attaching each head pad to the base plate.

15. The apparatus of claim 14 wherein the attaching means compromises:

cooperating hook and loop material carried on the bottom of each head pad and on the top surface of the base plate.

16. The apparatus of claim 1 further comprising:

strap means for immobilizing a victim's head between the head pads.

17. The apparatus of claim 16 wherein the strap means comprises:

at least one strap having opposed ends;

cooperating hook and loop material carried on each of the opposed ends of at the least one strap on each head.

18. The apparatus of claim 17 wherein:

each head pad has an inner side surface adapted to contact a victim's head and an opposed outer side surface;

the hook and loop material carried on the outer surface of each head pad.

19. The apparatus of claim 1 further comprising:

the base plate having spring action to bias the mounting members into engagement with a spine board.

20. A head immobilizing apparatus for use with a spine board having peripheral apertures, the head immobilizing apparatus comprising:

a base plate having a top plate surface and spaced side edges;

head pad means removably attached to the base plate, for restricting movement of a victim's head;

first and second clips carried on opposite side edges of the base plate and projecting outwardly therefrom, the first and second clips removably mounting the base plate to a spine board through apertures in a spine board; and an end clip carried on one end of the base plate between the two opposed side edges and adapted for releasable engagement with an aperture in an end of the spine board.

21. A head immobilizing apparatus for use with a spine board having peripheral apertures, the head immobilizing apparatus comprising:

a base plate having a concave top surface and spaced side edges;

head pad means removably attached to the base plate, for restricting movement of a victim's head;

first and second clips carried on opposite side edges of the base plate and projecting outwardly therefrom, the first and second clips removably mounting the base plate to a spine board through apertures in a spine board, each of the first and second clips including the first leg attached to and depending from one side edge of the base plate, and a second leg extending angularly from the first leg, the second leg extending at an acute angle with respect to the first leg; and wherein the base plate is laterally bendable about a longitudinal centerline to a planar shape as the first and second clips are inserted through apertures in a spine board into engagement with an outer edge of a spine board.

22. A head immobilizing apparatus for use with a spine board having peripheral apertures, the head immobilizing apparatus comprising:

a base plate having a top surface and spaced side edges;

head pad means removably attached to the base plate, for restricting movement of a victim's head;

first and second mounting members carried on opposite side edges of the base plate and projecting from a bottom surface of the base plate, the first and second mounting members removably mounting the base plate to a spine board through apertures in a spine board; each first and second mounting member formed of a leg depending from the bottom surface of the base plate and a projection extending inward from the leg toward a center of the base plate.

23. The apparatus of claim 22 wherein each leg is hollow.

24. The apparatus of claim 22 wherein the mounting members further comprise an end mounting member projecting from the bottom surface of the base plate adjacent a top end of the base plate.

25. The apparatus of claim 24 wherein the end mounting member further comprises:

a leg depending from the bottom surface of the base plate and a projection extending from the leg toward the opposite end of the base plate.

26. The apparatus of claim 22 wherein the base plate is concave between opposed side edges.

27. The apparatus of claim 22 wherein the side edges and a top end of the base plate project upwardly from a center portion of the base plate, the mounting members mounted adjacent the side edges and the top end of the base plate.

* * * * *